(12) United States Patent
Meeranpillai et al.

(10) Patent No.: US 12,072,346 B2
(45) Date of Patent: Aug. 27, 2024

(54) DETERMINING DEMULSIFIER PERFORMANCE

(71) Applicant: Saudi Arabian Oil Company, Dhahran (SA)

(72) Inventors: Nagoorpitchai S. Meeranpillai, Al Khobar (SA); Ali Almuhaimeed, Al-Qatif (SA); Osama Alzahrani, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 107 days.

(21) Appl. No.: 17/550,906

(22) Filed: Dec. 14, 2021

(65) Prior Publication Data
US 2023/0184654 A1 Jun. 15, 2023

(51) Int. Cl.
| | |
|---|---|
| *G01N 9/00* | (2006.01) |
| *C10G 33/06* | (2006.01) |
| *G01N 1/40* | (2006.01) |
| *G01N 13/02* | (2006.01) |
| *G01N 33/28* | (2006.01) |

(52) U.S. Cl.
CPC ............... *G01N 9/00* (2013.01); *C10G 33/06* (2013.01); *G01N 1/40* (2013.01); *G01N 13/02* (2013.01); *G01N 33/2823* (2013.01)

(58) Field of Classification Search
CPC ............ G01N 1/40; G01N 9/00; G01N 13/02; G01N 33/2823; G10G 33/06
See application file for complete search history.

(56) References Cited

U.S. PATENT DOCUMENTS

| | | | |
|---|---|---|---|
| 3,700,335 A | 10/1972 | Seelbinder | |
| 4,316,806 A * | 2/1982 | Canevari | C02F 1/682 |
| | | | 210/708 |
| 4,876,879 A | 10/1989 | Ruesch | |
| 5,381,002 A | 1/1995 | Morrow et al. | |
| 6,117,682 A | 9/2000 | Lynn et al. | |
| 7,468,402 B2 | 12/2008 | Yang et al. | |

(Continued)

OTHER PUBLICATIONS

U.S. Appl. No. 17/550,863, Meeranpillai et al., filed Dec. 14, 2021.
(Continued)

*Primary Examiner* — John Fitzgerald
(74) *Attorney, Agent, or Firm* — Fish & Richardson P.C.

(57) ABSTRACT

Tools, methods, and systems for evaluating a demulsifier performance from an emulsion mixture are described. The systems include a measuring instrument including a body with an open end, a cover attachable to the body, a sample holder sized to hold the emulsion mixture and to be received inside the body, the body and the cover define a sealable chamber; a sensor system positioned inside the sealable chamber an environmental control system positioned to enclose the sealable chamber; a data acquisition and processing system is in electronic communication with the sealable chamber, the sensor system, and the environmental control system. The sensor system includes a handle attached to and extruding from the cover of the measuring instrument; and a sensor loaded onto the handle, sized to be submerged inside the emulsion mixture of the sample holder, and operable to measure performance of the demulsifier.

20 Claims, 8 Drawing Sheets

(56) References Cited

U.S. PATENT DOCUMENTS

| | | | |
|---|---|---|---|
| 8,043,388 B2 | 10/2011 | Waters et al. | |
| 9,285,080 B2 | 3/2016 | Fan et al. | |
| 10,954,455 B1 | 3/2021 | Eggert et al. | |
| 11,105,722 B2* | 8/2021 | Kokal | G01N 11/04 |
| 11,262,281 B2* | 3/2022 | Kokal | G01N 21/85 |
| 11,458,533 B2* | 10/2022 | Chung | G01N 13/02 |
| 11,761,874 B2* | 9/2023 | AlSofi | G01N 33/2823 73/64.52 |
| 2018/0119031 A1 | 5/2018 | Haworth et al. | |
| 2019/0153304 A1 | 5/2019 | Zelenev | |
| 2019/0187034 A1 | 6/2019 | Lee et al. | |
| 2021/0348069 A1* | 11/2021 | White | C10G 33/04 |
| 2023/0184067 A1* | 6/2023 | Meeranpillai | E21B 43/12 166/250.01 |
| 2023/0266218 A1* | 8/2023 | Meeranpillai | G01N 13/02 73/32 R |
| 2023/0296581 A1* | 9/2023 | Sauerer | G01N 33/246 73/73 |

OTHER PUBLICATIONS

U.S. Appl. No. 17/679,582, Meeranpillai et al., filed Feb. 24, 2022.
U.S. Appl. No. 17/681,406, Meeranpillai, filed Feb. 25, 2022.
U.S. Appl. No. 17/681,576, Meeranpillai et al., filed Feb. 25, 2022.
Banda-Cruz et al., "Crude oil UV spectroscopy and light scattering characterization," Petroleum Science and Technology, Jun. 2016, 34(8):732-738, 7 pages.
Bastow, et al., "Ultraviolet spectroscopy for the analysis of oil-in-water effluent using isopropanol as co-solvent," Applied Spectroscopy, 1997, 51(3):319-322, 5 pages.
Chinaflo.com [online], "Oilfield Chemicals/DRA (Drag Reducing Agent) used for crude oil pipeline transportation," 2017, retried Oct. 1, 2021, retrieved from URL <https://www.chinafloc.com/DRA-Drag-reducing-agent-used-for-crude-oil-pipeline-transportation_1553.html>, 4 pages.
Civil-instruments-com.sell.everychina.com [online], "Demulsifer Performance Testing Instrument, Petroleum Testing Instrument," 2021, retrieved Oct. 1, 2021, retrief from URL <http://civil-instruments-com.sell.everychina.com/p-106461894-demulsifier-performance-testing-instrument-petroleum-testing-instrument.html>, 2 pages.
Dennington et al., "Miniaturized rotating disc rheometer test for rapid screen of draft reducing marine coatings," Surf. Topog.: Metrol. Prop., Sep. 2015, 10 pages.
Dynetesting.com [online], "Force Tensiometers," May 14, 2014, retrieved on Dec. 9, 2021 from URL <https://dynetesting.com/force-tensiometers/force-tensiometers-sigma-700-701/#squelch-taas-tab-content-0-4>, 8 pages.
Higgins, "Environmentally friendly oil in water analysis by FTIR spectroscopy based on ASTM D7678011," Agilent Technologies, 2012, retrieved from URL <https://www.perlan.com.pl/uploaded/AppBundleEntityProductApplication/fileKey/336/5990-9806enappnote630-4500-5500oilwater.pdf>, 6 pages.
Hong et al., "Rotating disk apparatus for polymer-induced turbulent drafg reduction," Journal of Mechanical Science and Technology, 2008, 22:1908-1913, 6 pages.
Kim et al., "A high-precision rotating disk apparatus for drag reduction characterization," Polymer Testing, 2001, 20:43-48, 6 pages.
Kruss-scientific.com [online], "Force Tensiometer—K100," retrieved on Dec. 9, 2021 from URL <https://www.kruss-scientific.com/en-US/products-services/products/k100?gclid=EAIaIQobChMI08y9yqDk9QIViBTUAR3m0Q7xEAAYASAAEgL1FPD_BwE>, 8 pages.
Kruss-scientific.com [online], "Tensiometer," retrieved on Dec. 9, 2021 from URL <https://www.kruss-scientific.com/en-US/know-how/glossary/tensiometer>, 5 pages.
Lawson-Wood et al., "FT-IR qualtification of hydrocarbons in environmental water samples based on ASTM D7678," 2015, retrieved from URL <https://labsense.fi/uploads/7/1/9/5/71957143/ft-ir_quantification_of_hydrocarbons_in_environmental_water_samples_based_on_astm_d7678_012499_01_app.pdf>, 4 pages.
Liquidpower.com [online], "About DRA and How it works," 2021, retrieved Oct. 1, 2021, retrieved from URL <https://www.liquidpower.com/what-is-dra/about-dra-and-how-it-works>, 3 pages.
Schatcogmbh.com [online], "Drag reducing agent (DRA)," retrieved on Feb. 3, 2022 from URL <https://schatcogmbh.com/product/drag-reducing-agent-dra/>, 2 pages.
Spectrosci.com [online], "Techniques for measuring oil in water," 2016, retrieved on Dec. 17, 2021 from URL <https://www.spectrosci.com/knowledge-center/resource-library/oil-in-water-and-soil>, 5 pages.

\* cited by examiner

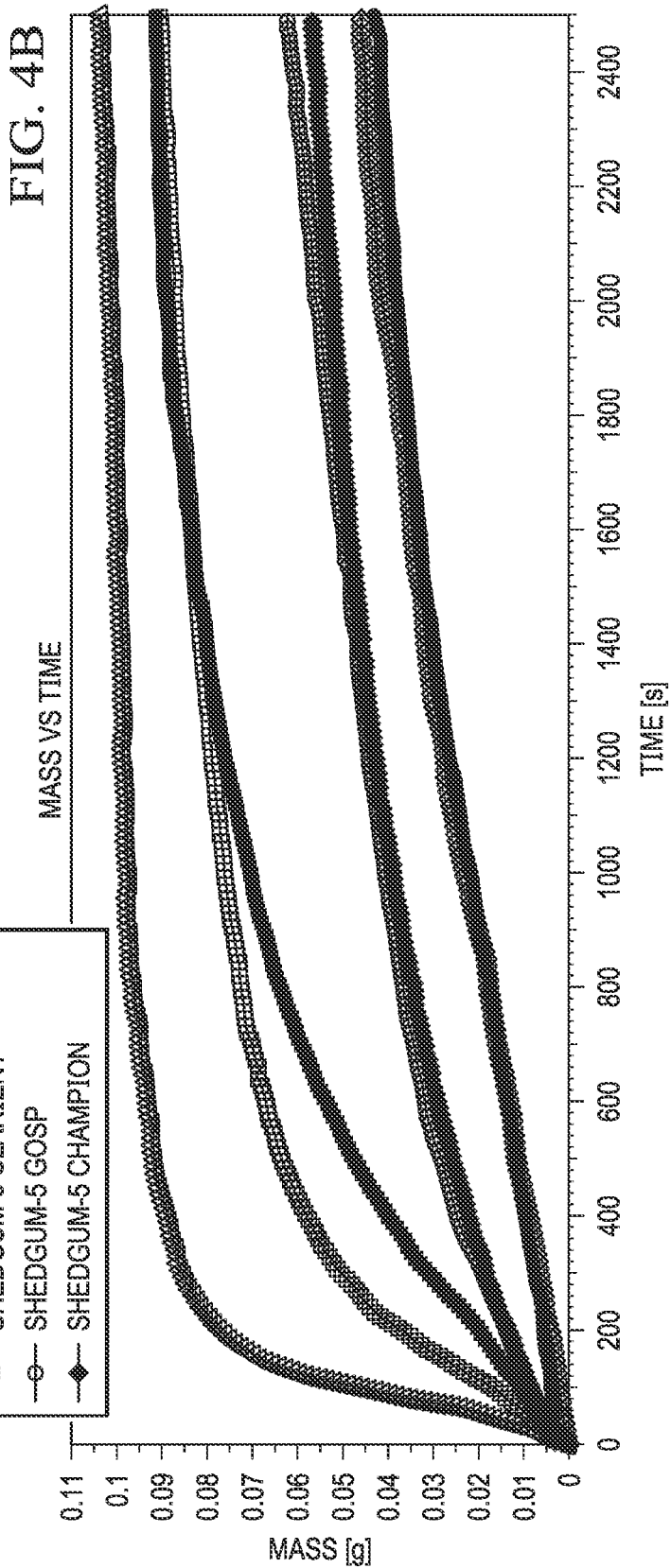

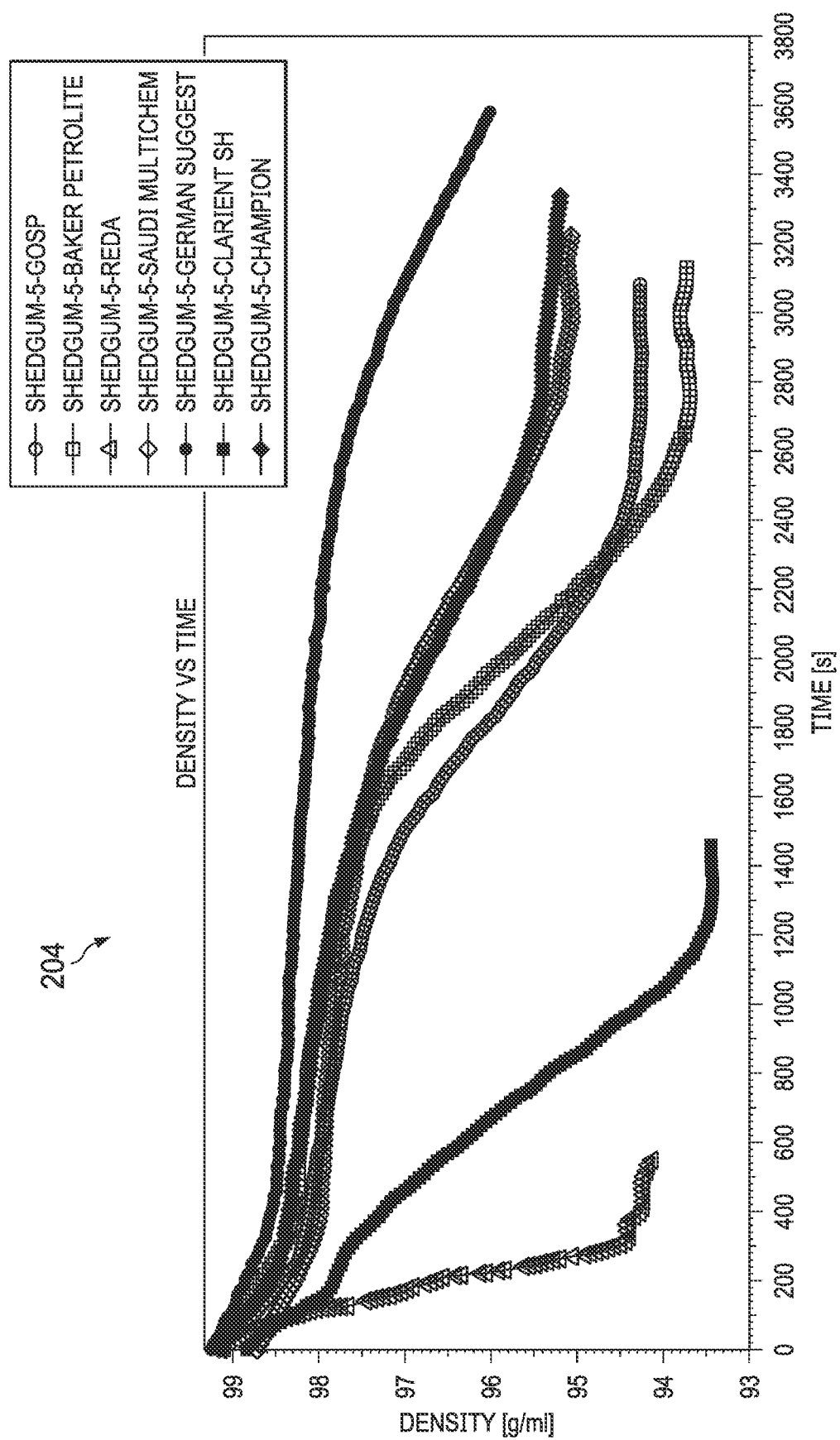

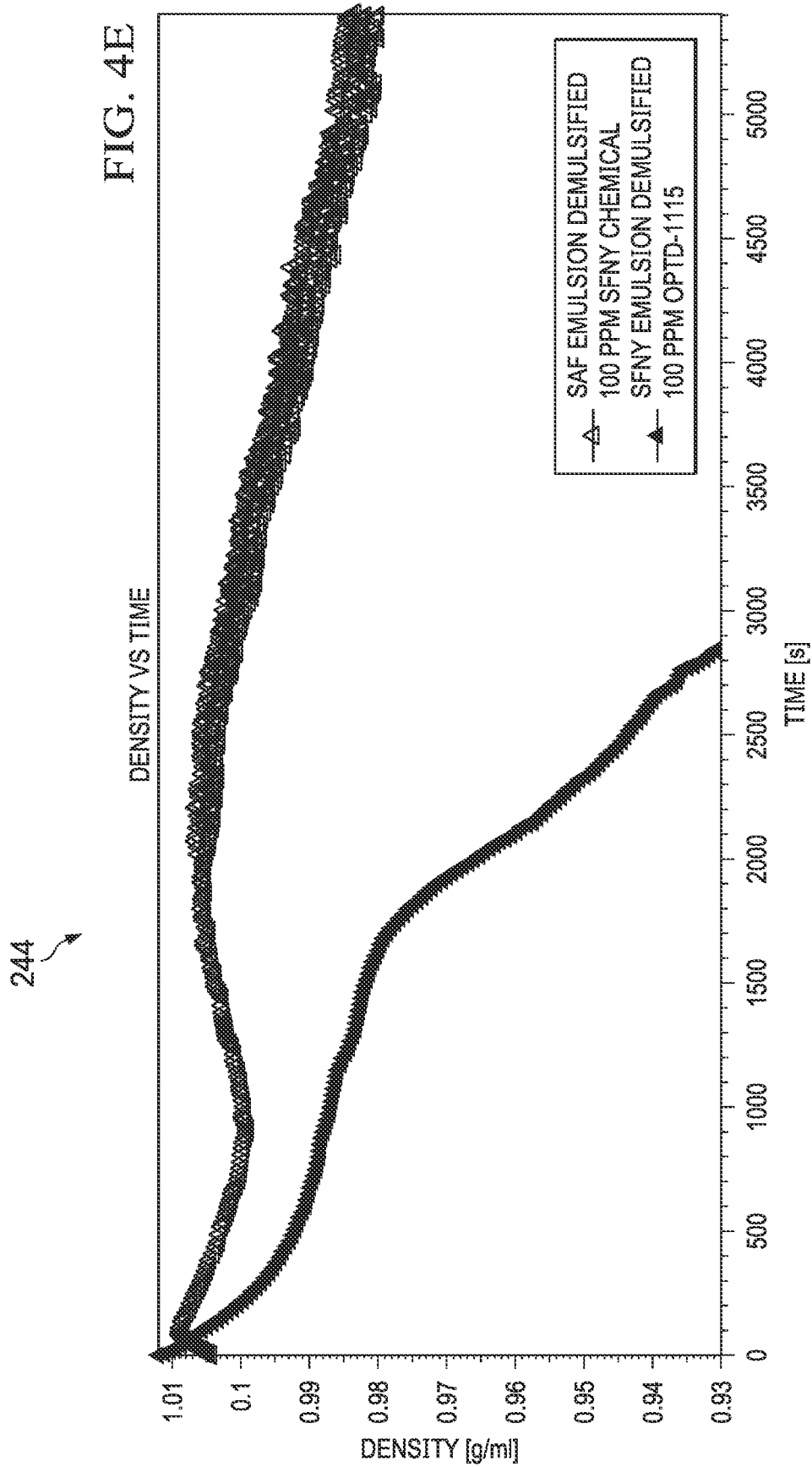

DETERMINING DEMULSIFIER PERFORMANCE

TECHNICAL FIELD

The present disclosure generally relates to tools, systems, and methods to evaluate performance of demulsifiers.

BACKGROUND

Demulsifiers, or emulsion breakers, are a special type of surfactant chemicals used in gas-oil-water-separation plants to facilitate separation of water from emulsified crude oil. The water can be removed from the crude oil prior to refining to prevent significant corrosion problems that can occur during the refining process.

The laboratory methods to evaluate demulsifiers' performance include bottle test methods. The bottle test methods include frequent human intervention to collect data and to observe test progress. The bottle test methods measure water separation from the crude oil.

SUMMARY

This specification describes tools, systems, and methods that can be used to test and evaluate the performance of different demulsifiers on separating water from crude oil. The test device can include a measuring instrument (e.g., Tensiometer), an environmental control system, a sensor system, and a data acquisition and processing system. The measuring instrument can measure a surface tension of liquid samples in Newton per meter (N/m). In this example, the measuring instrument includes a probe (i.e., sensor) and measures a tensile force that is produced as a result of wetting the submerged probe (i.e., sensor) with respect to the wetted length of the probe. The probe can be a ring or a plate (e.g., duNouy ring or Wilhelmy plate). The probe can include a platinum metal material. The measuring instrument can measure the density of a liquid using Archimedes principle. In this example, the Archimedes principle is used to measure density for non-homogeneous crude oil and water mixtures (e.g., crude oil emulsions). The measuring instrument includes a hook that connects the measuring instrument with the measuring probe. The probe has a cylindrical shape and includes a Teflon™ material. Teflon™ has a non-sticky nature with water from crude oil emulsions. In some implementations, a water non-stick probe is used. In some implementations, the probe can include a nanoparticle coating with sensing capability for determining the density of crude oil emulsions. The measuring instrument includes a sample holder where the sample is placed for measurements. For example, the sample holder can include a glass beaker with a volume of 100 ml, an internal diameter of 6.3 cm, and an internal height of 3.4 cm. The sample holder and a cover can be attached to a body of the measuring instrument. The body and the cover can form a sealable chamber when connected while measuring. The sample holder is covered during testing. In use, the emulsion sample holder is seated inside the body of the sealable chamber. The emulsion sample holder contains a mixture of crude oil and demulsifier chemical during testing. After transfer of the crude emulsion and addition of the demulsifier, the mixture is mixed with a magnetic stirrer until homogeneity of the solution is achieved. The mixing time is preset by the user. A sensor is attached to the probe of the measuring instrument. Initially, the sensor is set at rest to prevent oscillation and inaccuracy of the instrument. In operation, the sensor system is submerged into the mixture inside the emulsion sample holder. The environmental control system includes a set of elements that regulate temperature around the sealable chamber.

The sensor system includes sensors, instrumentation and signal processing circuits, receivers, transmitters, and data storing and processing devices. The sensor system acquires real-time measurement data of the mixture sample and transfers it to the data acquisition and processing system for analysis and calculations.

The tools, systems, and methods described in this specification can accurately evaluate demulsifier performance on separating wet-crude emulsions into oil and water. Specifically, this method measures emulsion density, during the separation test, using a tensiometer with a sensing system. The sensing system is designed for non-wetting applications (e.g., water-wet systems). The method allows the tensiometer to run the experiment automatically. This measuring approach is simple with increased accuracy.

By analyzing demulsifier performance, this approach can enable selection of an appropriate demulsifier and prevent process deviations related to poor water separation. The process can reduce bottle necking of gas-oil-water-separation plants due to higher water-cut issues (i.e., water-cut is the ratio of produced water compared to the volume of the total produced fluids in a well) and reduce excess addition of costly oil field chemicals. The automated method can reduce error in data collection associated with human interaction that can occur during sample preparation, shearing/mixing, direct reading of volume of water, and time management. The method automatically measures demulsifiers' performance and ranks them once the data is collected. The results and technical reports can be sent directly to the customers without lengthy analysis.

In some aspects, a system for evaluating a demulsifier performance from an emulsion mixture includes a measuring instrument including a body with an open end, a cover attachable to the body, a sample holder sized to hold the emulsion mixture and to be received inside the body, the body and the cover define a sealable chamber; a sensor system positioned inside the sealable chamber, an environmental control system positioned to enclose the sealable chamber; and a data acquisition and processing system is in electronic communication with the sealable chamber, the sensor system, and the environmental control system. The sensor system includes a handle attached to and extruding from the cover of the measuring instrument; and a sensor loaded onto the handle, sized to be submerged inside the emulsion mixture of the sample holder, and operable to measure performance of the demulsifier.

Embodiments of the system for evaluating a demulsifier performance from an emulsion mixture can include one or more of the following features.

In some embodiments, the emulsion mixture includes a demulsifier and crude oil. In some cases, the crude oil is light or heavy crude oil or combination thereof.

In some embodiments, the measuring instrument is a tensiometer.

In some embodiments, the sensor is a rectangular plate.

In some embodiments, the sensor is a cylinder.

In some embodiments, the sensor includes a non-stick based coating material operable to measure properties for non-wet applications. In some cases, the non-stick based coating material is Teflon™ and the sensor is operable to measure a density of a liquid. The liquid can be a petroleum crude oil emulsions.

In some embodiments, the sensor includes a metal or plastic based material with a nanomaterial coating. In some cases, the sensor is a hydrophobic sensor.

In some embodiments, the data acquisition and processing system includes user interface operable to display graphical results from testing.

In some embodiments, the environmental control system includes elements to control temperature during testing.

In some aspects, a method for evaluating a demulsifier performance from an emulsion mixture includes loading the emulsion mixture into a sample holder of a measuring instrument; lowering a sensing system attached to a cover of the measuring instrument into the emulsion mixture, the sensing system includes a sensor; submerging the sensor of the sensing system completely into the emulsion mixture; calculating the change in density of the emulsion mixture as a demulsification process takes place inside the measuring instrument; displaying a plurality of graphical results on a user interface using a data acquisition and processing system; and ranking the performance of each demulsifier from the plurality of demulsifiers used for testing.

Embodiments of the method for evaluating a demulsifier performance from an emulsion mixture can include one or more of the following features.

In some embodiments, the method includes mixing an emulsion liquid with a demulsifier to form the emulsion mixture.

In some embodiments, the method includes demulsification process of the emulsion mixture where the water separates from the oil and settles due to gravity.

In some embodiments, the method includes detecting change in density from the emulsion mixture and calculating density values using Archimedes' principle. In some cases, calculating density values for each emulsion mixture including a demulsifier from the plurality of demulsifiers. In some cases, processing the density values for each emulsion mixture including a demulsifier using a data acquisition and processing system. In some cases, displaying a change in density values over time for each emulsion mixture including a demulsifier on a user interface.

In some embodiments, the method includes ranking the performance of each demulsifier by classifying each demulsifier as strong or weak demulsifier.

In some embodiments, the method includes evaluating the demulsifier performance from an emulsion mixture by calculating a water separation.

This approach collects measurements on emulsion separation behavior, density reduction (i.e., desalting) performance every fraction of a second, and can be used in various applications. The success rate of the described automated method in identifying the demulsifiers' performance is improved (e.g., 75% success rate with the described approach compared to 25% success rate using the bottle test methods). The described method provides real-time data interpretation under low operating temperature conditions and integrates changing conditions such as flow rate, water-cut, and temperature.

The details of one or more embodiments of these systems and methods are set forth in the accompanying drawings and the description below. Other features, objects, and advantages of these systems and methods will be apparent from the description, drawings, and the claims.

DESCRIPTION OF DRAWINGS

FIGS. 4A-4E are example charts of measured demulsifiers' performance in various crude oils.

DETAILED DESCRIPTION

Figure 1:
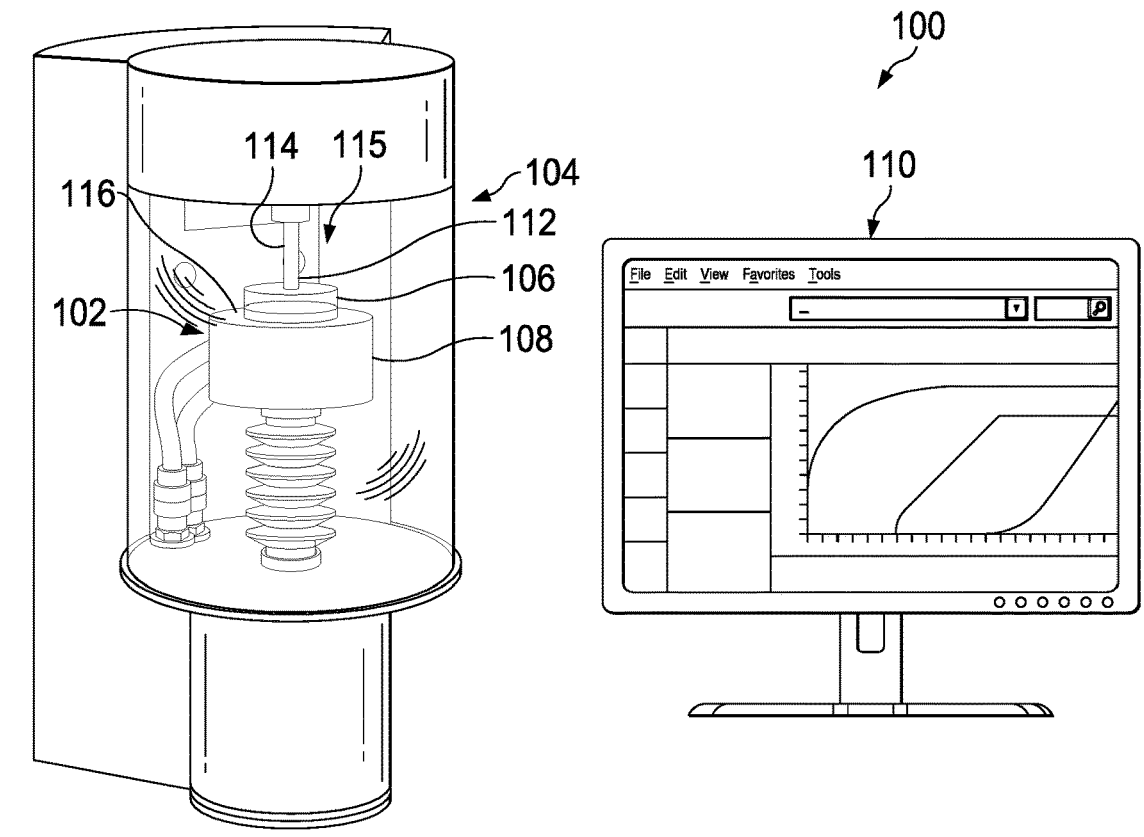
FIG. 1 is a schematic of an automated test tool that includes a tensiometer.

This specification describes tools, systems, and methods that can be used to test and evaluate the performance of different demulsifiers on separating water from crude oil. The test device can include a measuring instrument (e.g., Tensiometer), an environmental control system, a sensor system, and a data acquisition and processing system. The measuring instrument can measure a surface tension of liquid samples in Newton per meter (N/m). In this example, the measuring instrument includes a probe (i.e., sensor) and measures a tensile force that is produced as a result of wetting the submerged probe (i.e., sensor) with respect to the wetted length of the probe. The probe can be a ring or a plate (e.g., Du Noüy ring or Wilhelmy plate). The probe can include a platinum metal material. The measuring instrument can measure the density of a liquid using Archimedes principle. In this example, the Archimedes principle is used to measure density for non-homogeneous crude oil and water mixtures (e.g., crude oil emulsions). The measuring instrument includes a hook that connects the measuring instrument with the measuring probe. The probe has a cylindrical shape and includes a Teflon™ material. Teflon™ has a non-sticky nature with water from crude oil emulsions. In some implementations, a water non-stick probe is used. In some implementations, the probe can include a nanoparticle coating with sensing capability for determining the density of crude oil emulsions. The measuring instrument includes a sample holder where the sample is placed for measurements. For example, the sample holder can include a glass beaker with a volume of 100 ml, an internal diameter of 6.3 cm, and an internal height of 3.4 cm. The sample holder and a cover 116 can be attached to a body 108 of the measuring instrument. The body 108 and the cover 116 can form a sealable chamber when connected while measuring. The sample holder is covered during testing. In use, the emulsion sample holder is seated inside the body of the sealable chamber. The emulsion sample holder contains a mixture of crude oil and demulsifier chemical during testing. After transfer of crude emulsion and addition of demulsifier, the mixture is mixed with a magnetic stirrer until homogeneity of the solution is achieved. The mixing time is preset by the user. A sensor is attached to the probe of the measuring instrument. Initially, the sensor is set at rest to prevent oscillation and inaccuracy of the instrument. In operation, the sensor system is submerged into the mixture inside the emulsion sample holder. The environmental control system includes a set of elements that regulate temperature around the sealable chamber.

The sensor system includes sensors, instrumentation and signal processing circuits, receivers, transmitters, and data storing and processing devices. The sensor system acquires real-time measurement data of the mixture sample and transfers it to the data acquisition and processing system for analysis and calculations.

The tools, systems, and methods described in this specification can accurately evaluate demulsifier performance on separating wet-crude emulsions into oil and water. Specifically, this method measures emulsion density, during the separation test, using a tensiometer with a sensing system. The sensing system is designed for non-wetting applications (e.g., water-wet systems). The method allows the tensiometer to run the experiment automatically. This measuring approach is simple with increased accuracy.

FIG. 1 is a schematic of an automated test device 100 that includes a tensiometer 102. The automated test device 100 allows screening of various demulsifiers for wet-crude emulsions. The described tool and approach is applicable for water-cuts measurements with a range between 5 and 80%. Automating the test tool 100 allows usage of the same demulsifier with the same crude oil by preserving the efficiency of the demulsifier, including the changes of the fluid characteristics. In the illustrated test tool, the tensiometer 102 is enclosed in an environmental control system 104. In some implementations, the tensiometer can be a separate unit from the environmental control system. In preparation for testing, the mixture of the crude oil and the demulsifier is poured into a cup or sample holder 106 that is placed into the body 108 of the tensiometer 102. Once testing parameters are set by the user using the data acquisition and processing system 110, the sensor system 115 including the sensor 112 attached on a handle 114 is submerged into the cup 106 that contains the mixture.

Figure 2A:
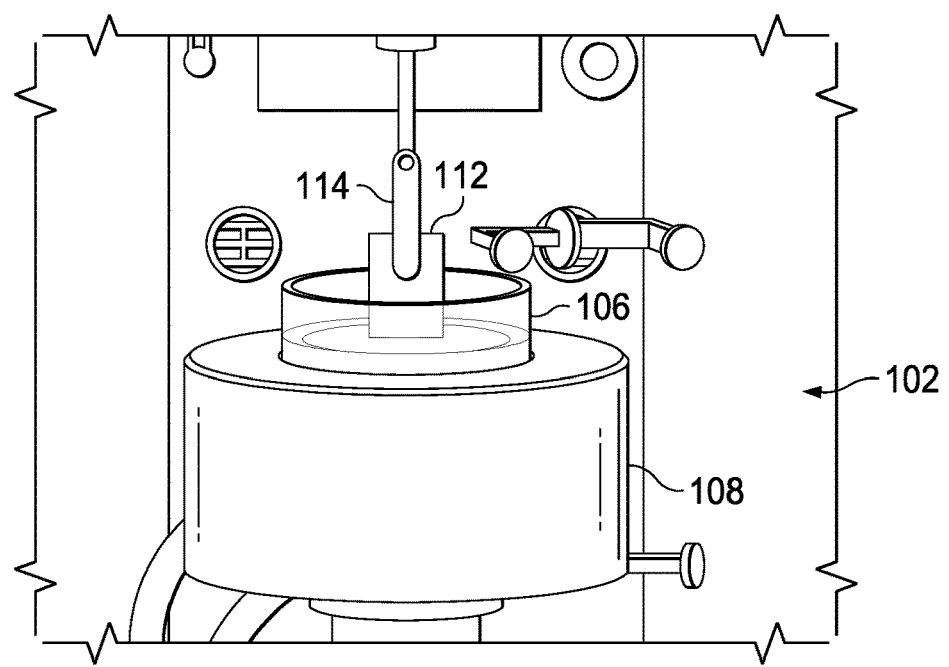
FIGS. 2A-2B are schematic views of the tensiometer including a sensor
Figure 2B:
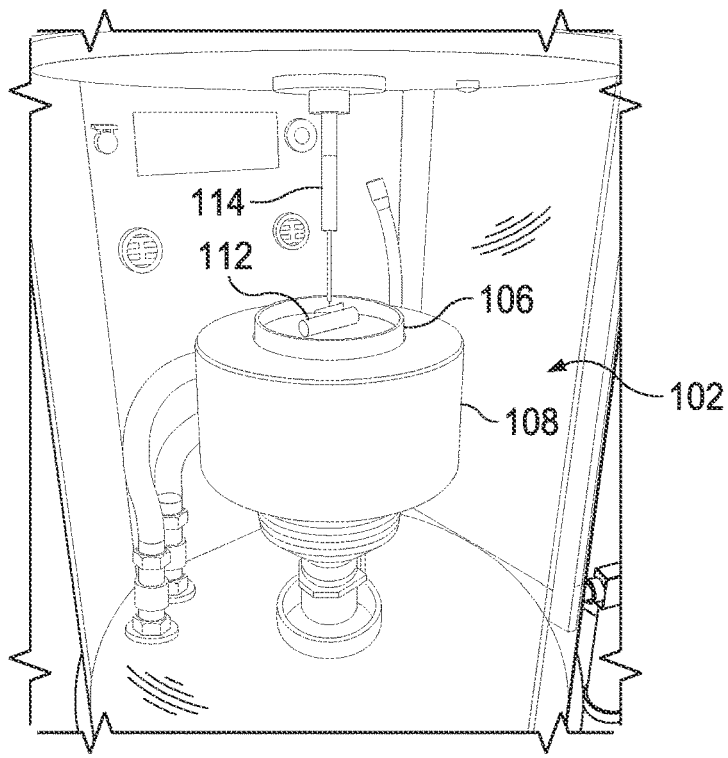

FIGS. 2A-2B are schematic views of the tensiometer 102 including the sensor 112. In some implementations, the sensor 112 is a rectangular plate (FIG. 2A). In some implementations, the sensor 112 is a cylinder (FIG. 2B). The cylindrical sensor 112 can include a non-stick based coating material (e.g., polytetrafluoroethylene (PTFE) or Teflon™) with properties for non-wet applications. This allows the sensor 112 to measure the density of a liquid for example, petroleum crude oil emulsion. Water from emulsion will not stick on a Teflon™ surface and the separated water will settle down by gravity. The change in density from the emulsion mixture to a clean crude oil can be automatically detected, calculated, and displayed on a user interface. In some examples, the cylindrical sensor 112 can include a metal or plastic based material with a nanomaterial coating (e.g., a hydrophobic sensor). A sensor with a nanomaterial coating can improve the quality of the demulsifiers' performance tests. Nanomaterial coated parts have high hydrophobic characteristics (i.e., non-wetting lotus effect characteristics).

Figure 3:
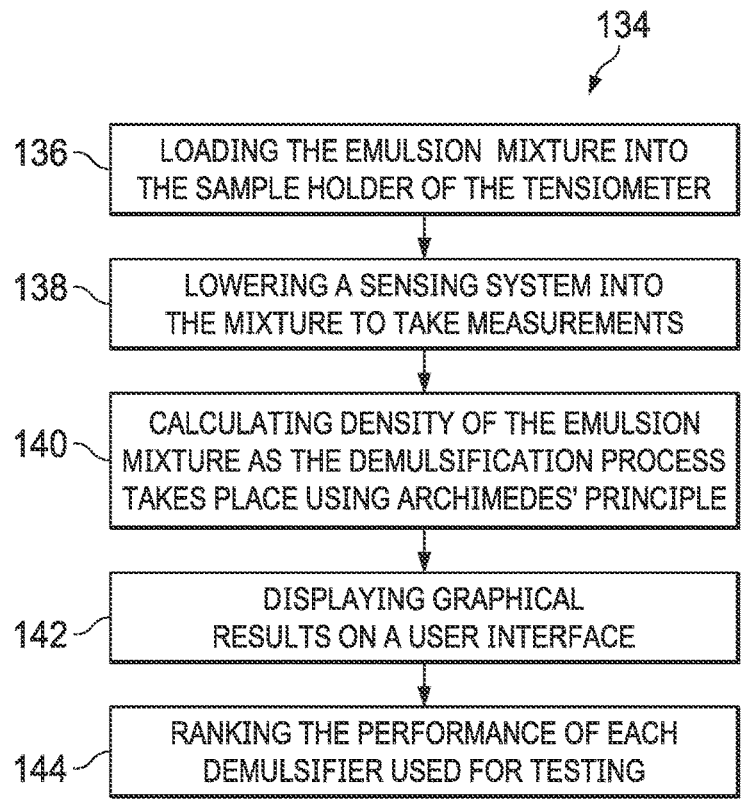
FIG. 3 is a flow chart of a method for determining demulsifier performance.
Figure 4A:
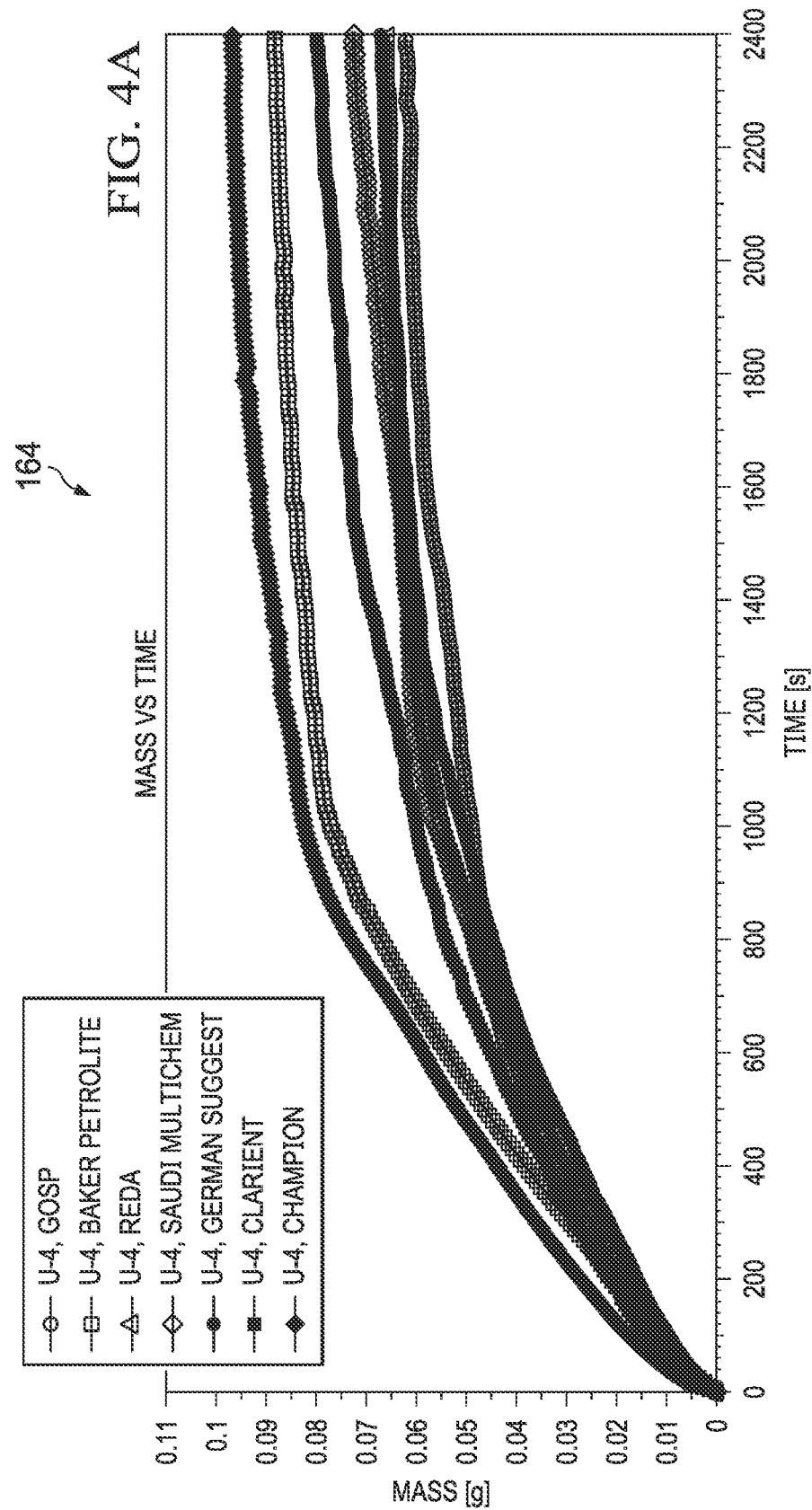
Figure 4D:
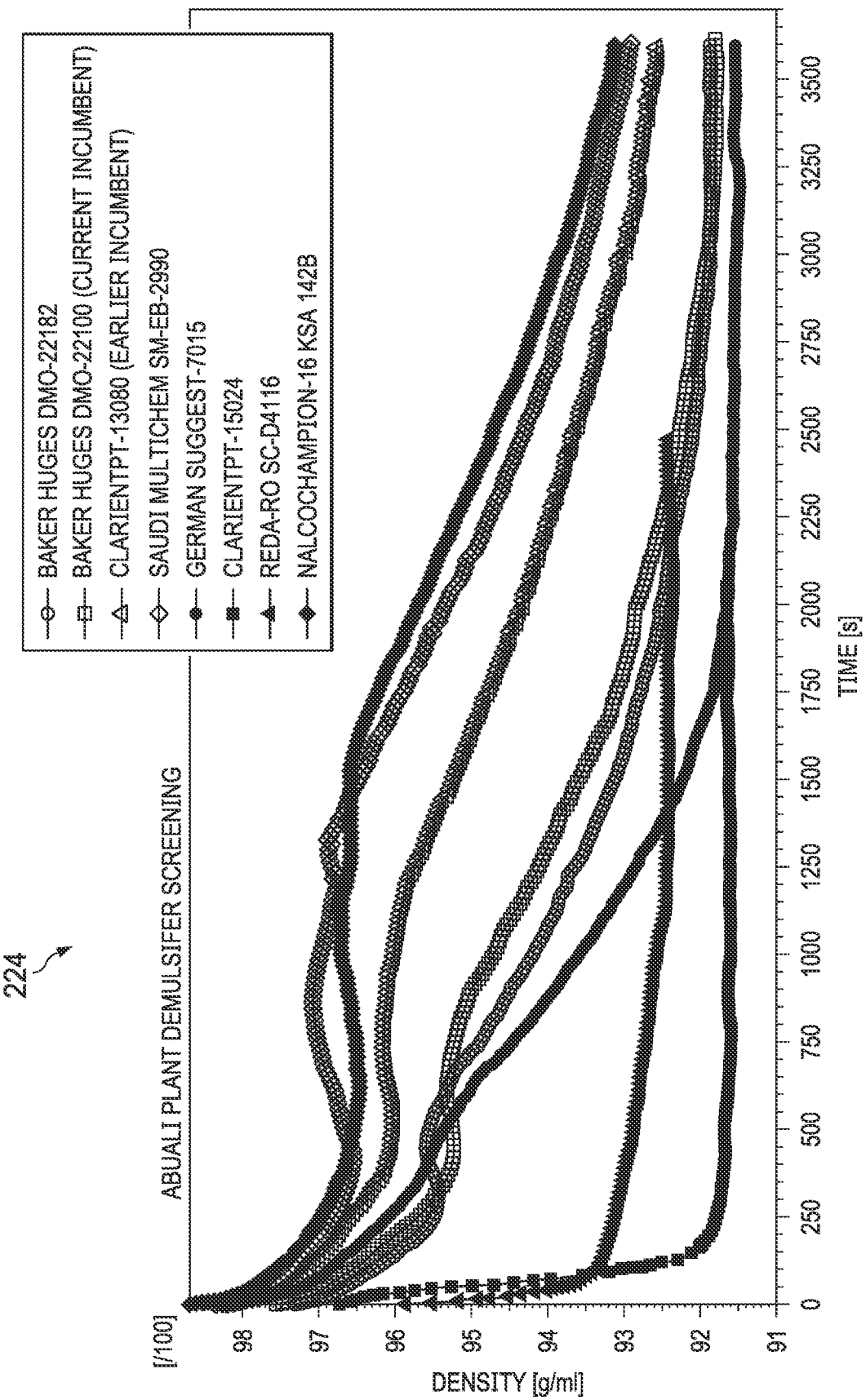

FIG. 3 is a flow chart of a method 134 for determining demulsifier performance. At step 136, the emulsion mixture including the crude oil and the demulsifier are loaded into the sample holder 106 of the tensiometer 102 as described earlier in reference to FIG. 1. At step 138, a sensing system 115, including a Teflon™ coated cylinder 112, is submerged into the emulsion mixture. The time of submersion is programmed into the data acquisition and processing system 110 by a user. The length of time depends on the type of crude oil used for each experiment. For example, for light crude oil, the sensor 112 can measure the density reduction between 15 and 20 minutes. In heavy crude oil, the sensor 112 can measure the density reduction between 40 and 60 minutes. The length of time can also depend on the type and efficiency of the demulsifier present in the crude oil. For example, if the demulsifier is strong, the measurements can be collected over a shorter time. If the demulsifier is weak the measurements can be collected in longer time. The described method 134 can measure the demulsifier's performance in light or heavy types of crude oil. At step 140, the sensing system 115 measures emulsion density reduction before and after treatment of the liquid with a demulsifier. The change in density is calculated based on Archimedes' principle using Equation 1

$$F_b = -\rho g V \quad \text{Eq. (1)}$$

where $F_b$ is a buoyant force, $\rho$ is the density of the fluid, g is acceleration due to gravity, and V is volume of the fluid. In this example, the Archimedes' principle is used to measure the density of the non-homogeneous crude oil and water mixture (e.g., crude oil emulsions). The buoyance buoyant force is the difference between the weight of the body in air and the weight of the body in water. This is equal to the density of the fluid multiplied by the acceleration due to gravity and then multiplied by the volume of the object. At step 142, the density reduction measurements are transferred in-situ and graphically displayed on a user interface by the data acquisition and processing system 110. For example, graphical results can be displayed on a chart distribution with mass measured in grams or density measured in grams per milliliter and time measured in seconds. If the density over time relationship of the chart decreases, then the performance of the demulsifier is strong. If the density over time relationship of the chart increases, then the performance of the demulsifier is weak. At the start of the testing, it is often evident that the emulsion density is higher and with a strong performing demulsifier the density can gradually and quickly decrease.

At step 144, the graphical distribution helps the user to rank the demulsifiers based on the reduction in emulsion density over time. Table 1 shows an example of demulsifier ranking using the automated test tool 100 in the lab compared to ranking performed at the field.

FIGS. 4A-4E are example charts 164, 184, 204, 224, 244 of measured demulsifiers' performance in various crude oils. The charts show screening of demulsifiers from various suppliers such as Baker Petrolite, GOSP, REDA, Saudi Multichem, German Suggest, Clarient, Champion. The various demulsifiers were tested, on several crude emulsion mixtures, directly on the field or brought in the lab from the field (e.g., Hawiyah Gas Plant, Shedgum Gas Plant, and Abuali Gas Plant). A graphical display of data illustrates the efficiency of different demulsifiers. The results match, which confirms the accuracy of the described approach. For example, the strongest demulsifiers, Baker Petrolit, Clarient, and Champion were rated as top three with the described method as well as with the field ranking approach.

| Product (Supplier) | Field Trail Ranking | New Method Ranking |
|---|---|---|
| Baker Petrolit | 1 (13.8 PPM) | 2 |
| Clarient | 2 (14.6 PPM) | 3 |
| Champion | 3 (17.8 PPM) | 1 |
| GOSP | 4 (17.9 PPM) | 4 |
| Saudi Multichem | 5 (30.9 PPM) | 5 |
| REDA | 6 (31.2 PPM) | 6 |
| German Suggest | 7 (N/A) | 7 |

Table 2 shows an example of various demulsifiers ranking using the described approach at lower temperature (e.g., 80° F.) instead of higher temperatures (e.g., >100° F.) used by current methods. The ranking using the described approach shows approved accuracy over the conventional methods.

| Tensiometer method at 80° F. | | ESI method at 100° F. | | ESI method at 132° F. | |
|---|---|---|---|---|---|
| Product | Ranking | Product | Ranking | Product | Ranking |
| REDA | 1 | Baker Petrolit | 1 | Baker Petrolit | 1 |
| Baker Petrolit | 2 | Clarient | 2 | Clarient | 2 |
| Clarient | 3 | REDA | 3 | REDA | 3 |
| GOSP | 4 | Champion | 4 | Champion | 4 |
| Champion | 5 | GOSP | 5 | GOSP | 5 |
| Saudi Multichem | 6 | German Suggest | 6 | German Suggest | 6 |
| German Suggest | 7 | Saudi Multichem | 7 | Saudi Multichem | 7 |

Figure 5:
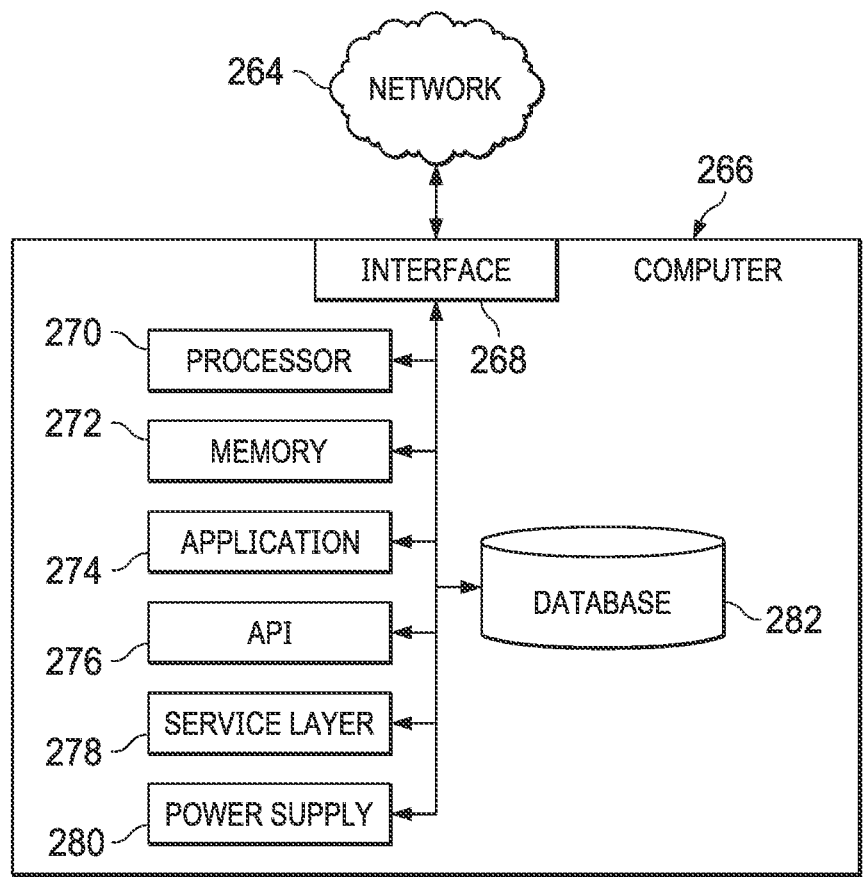
FIG. 5 is a block diagram of an example computer system.

FIG. 5 is a block diagram of an example computer system 266 used to provide computational functionalities associated with described algorithms, methods, functions, processes, flows, and procedures described in the present disclosure, according to some implementations of the present disclosure. The illustrated computer 266 is intended to encompass any computing device such as a server, a desktop computer, a laptop/notebook computer, a wireless data port, a smartphone, a personal data assistant (PDA), a tablet computing device, or one or more processors within these devices, including physical instances, virtual instances, or both. The computer 266 can include input devices such as keypads, keyboards, and touch screens that can accept user information. Also, the computer 266 can include output devices that can convey information associated with the operation of the computer 266 The information can include digital data, visual data, audio information, or a combination of information. The information can be presented in a graphical user interface (UI) (or GUI).

The computer 266 can serve in a role as a client, a network component, a server, a database, a persistency, or components of a computer system for performing the subject matter described in the present disclosure. The illustrated computer 266 is communicably coupled with a network 264. In some implementations, one or more components of the computer 266 can be configured to operate within different environments, including cloud-computing-based environments, local environments, global environments, and combinations of environments.

At a high level, the computer 266 is an electronic computing device operable to receive, transmit, process, store, and manage data and information associated with the described subject matter. According to some implementations, the computer 266 can also include, or be communicably coupled with, an application server, an email server, a web server, a caching server, a streaming data server, or a combination of servers.

The computer 266 can receive requests over network 264 from a client application (for example, executing on another computer 266). The computer 266 can respond to the received requests by processing the received requests using software applications. Requests can also be sent to the computer 266 from internal users (for example, from a command console), external (or third) parties, automated applications, entities, individuals, systems, and computers. Each of the components of the computer 266 can communicate using a system bus 564. In some implementations, any or all of the components of the computer 266, including hardware or software components, can interface with each other or the interface 268 (or a combination of both), over the system bus 564. Interfaces can use an application programming interface (API) 276, a service layer 278, or a combination of the API 276 and service layer 278. The API 276 can include specifications for routines, data structures, and object classes. The API 276 can be either computer-language independent or dependent. The API 276 can refer to a complete interface, a single function, or a set of APIs.

The service layer 278 can provide software services to the computer 266 and other components (whether illustrated or not) that are communicably coupled to the computer 266. The functionality of the computer 266 can be accessible for all service consumers using this service layer. Software services, such as those provided by the service layer 278, can provide reusable, defined functionalities through a defined interface. For example, the interface can be software written in JAVA, C++, or a language providing data in extensible markup language (XML) format. While illustrated as an integrated component of the computer 266, in alternative implementations, the API 276 or the service layer 278 can be stand-alone components in relation to other components of the computer 266 and other components communicably coupled to the computer 266. Moreover, any or all parts of the API 276 or the service layer 278 can be implemented as child or sub-modules of another software module, enterprise application, or hardware module without departing from the scope of the present disclosure.

The computer 266 includes an interface 268. Although illustrated as a single interface 268 in FIG. 5, two or more interfaces 268 can be used according to particular needs, desires, or particular implementations of the computer 266 and the described functionality. The interface 268 can be used by the computer 266 for communicating with other systems that are connected to the network 264 (whether illustrated or not) in a distributed environment. Generally, the interface 268 can include, or be implemented using, logic encoded in software or hardware (or a combination of software and hardware) operable to communicate with the network 264. More specifically, the interface 268 can include software supporting one or more communication protocols associated with communications. As such, the network 264 or the interface's hardware can be operable to communicate physical signals within and outside of the illustrated computer 266.

The computer 266 includes a processor 270. Although illustrated as a single processor 270 in FIG. 5, two or more processors 270 can be used according to particular needs, desires, or particular implementations of the computer 266 and the described functionality. Generally, the processor 270 can execute instructions and can manipulate data to perform the operations of the computer 266, including operations using algorithms, methods, functions, processes, flows, and procedures as described in the present disclosure.

The computer 266 also includes a database 282 that can hold data for the computer 266 and other components connected to the network 264 (whether illustrated or not). For example, database 282 can be an in-memory, conventional, or a database storing data consistent with the present disclosure. In some implementations, database 282 can be a combination of two or more different database types (for example, hybrid in-memory and conventional databases) according to particular needs, desires, or particular implementations of the computer 266 and the described functionality. Although illustrated as a single database 282 in FIG. 5, two or more databases (of the same, different, or combination of types) can be used according to particular needs, desires, or particular implementations of the computer 266 and the described functionality. While database 282 is illustrated as an internal component of the computer 266, in alternative implementations, database 282 can be external to the computer 266.

The computer 266 also includes a memory 272 that can hold data for the computer 266 or a combination of components connected to the network 264 (whether illustrated or not). Memory 272 can store any data consistent with the present disclosure. In some implementations, memory 272 can be a combination of two or more different types of memory (for example, a combination of semiconductor and magnetic storage) according to particular needs, desires, or particular implementations of the computer 266 and the described functionality. Although illustrated as a single memory 272 in FIG. 5, two or more memories 272 (of the same, different, or combination of types) can be used according to particular needs, desires, or particular implementations of the computer 266 and the described functionality. While memory 272 is illustrated as an internal component of the computer 266, in alternative implementations, memory 272 can be external to the computer 266.

The application 274 can be an algorithmic software engine providing functionality according to particular needs, desires, or particular implementations of the computer 266 and the described functionality. For example, application 274 can serve as one or more components, modules, or applications. Further, although illustrated as a single application 274, the application 274 can be implemented as multiple applications 274 on the computer 266. In addition, although illustrated as internal to the computer 266, in alternative implementations, the application 274 can be external to the computer 266.

The computer 266 can also include a power supply 280. The power supply 280 can include a rechargeable or non-rechargeable battery that can be configured to be either user- or non-user-replaceable. In some implementations, the power supply 280 can include power-conversion and management circuits, including recharging, standby, and power management functionalities. In some implementations, the power-supply 280 can include a power plug to allow the computer 266 to be plugged into a wall socket or a power source to, for example, power the computer 266 or recharge a rechargeable battery.

There can be any number of computers 266 associated with, or external to, a computer system containing computer 266, with each computer 266 communicating over network 264. Further, the terms "client," "user," and other appropriate terminology can be used interchangeably, as appropriate, without departing from the scope of the present disclosure. Moreover, the present disclosure contemplates that many users can use one computer 266 and one user can use multiple computers 266.

Implementations of the subject matter and the functional operations described in this specification can be implemented in digital electronic circuitry, intangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially-generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A system for evaluating a demulsifier performance from an emulsion mixture comprising a demulsifier, the system comprising:
   a tensiometer configured to sense a buoyant force of the emulsion mixture, the tensiometer comprising:
      a body with an open end;
      a cover attachable to the body;
      a sample holder sized to hold the emulsion mixture and the demulsifier, the sample holder sized to be received inside the body, wherein the body and the cover define a sealable chamber;
      a handle attached to and extruding from the cover; and
      a probe loaded onto the handle, the probe sized to be submerged inside the emulsion mixture in the sample holder below the cover, the emulsion mixture exerting the buoyant force on the probe when the probe is submerged inside the emulsion mixture;
   an environmental control system positioned to enclose the tensiometer; and
   a data acquisition and processing system in electronic communication with the tensiometer, and the environmental control system, the data acquisition and processing system configured to perform operations comprising:
      receiving a signal representing the buoyant force of the emulsion mixture from the tensiometer; and
      based on the buoyant force of the emulsion mixture, determining the demulsifier performance of the demulsifier.

2. The system of claim 1, wherein the probe sensor comprises a rectangular plate.

3. The system of claim 1, wherein the probe comprises a cylinder.

4. The system of claim 1, wherein the data acquisition and processing system comprises a user interface operable to display graphical results from testing.

5. The system of claim 1, wherein the environmental control system comprises elements to control temperature during testing.

6. The system of claim 1, wherein the emulsion mixture comprises a demulsifier and a crude oil.

7. The system of claim 6, wherein the crude oil comprises at least one of a light crude oil, a heavy crude oil, or a combination thereof.

8. The system of claim 1, wherein the probe comprises a non-stick based coating material, the non-stick based coating material having non-wetting lotus effect characteristics.

9. The system of claim 8, wherein the non-stick based coating material comprises a fluoropolymer, the probe operable to measure a density of a liquid, wherein the liquid comprises a petroleum crude oil emulsion.

10. The system of claim 1, wherein the probe comprises at least one of a metal or a plastic based material with a nanomaterial coating.

11. The system of claim 10, wherein the probe comprises a hydrophobic sensor.

12. A method for evaluating a demulsifier performance from an emulsion mixture, the method comprising:
   loading the emulsion mixture into a sample holder of a tensiometer;
   lowering a probe of the tensiometer attached to a cover of the tensiometer by a handle of the tensiometer into the emulsion mixture with the sample holder received inside a body of the tensiometer;
   submerging the probe completely into the emulsion mixture;
   measuring a change in a buoyant force exerted on the probe by the emulsion mixture as a demulsification process takes place on the emulsion mixture;
   based on the change in the buoyant force, calculating a change in density of the emulsion mixture as a demulsification process takes place;
   performing the demulsification process for each demulsifier of a plurality of demulsifiers with the emulsion mixture;
   responsive to performing the demulsification process for each demulsifier of the plurality of demulsifiers with the emulsion mixture, determining the demulsifier performance for each demulsifier of the plurality of demulsifiers;
   displaying a plurality of graphical results of the demulsifier performance of each of the plurality of demulsifiers on a user interface of a data acquisition and processing system; and
   ranking the demulsifier performance of each demulsifier from the plurality of demulsifiers used for testing.

13. The method of claim 12, comprising mixing, using the probe, an emulsion liquid with the demulsifier to form the emulsion mixture.

14. The method of claim 12, further comprising performing the demulsification process with the emulsion mixture, the emulsion mixture comprising water and oil, wherein the water separates from the oil and settles due to gravity.

15. The method of claim 12, wherein ranking the demulsifier performance of each demulsifier further comprising classifying each demulsifier as a strong or a weak demulsifier.

16. The method of claim 12, wherein evaluating the demulsifier performance from the emulsion mixture further comprising calculating a water separation.

17. The method of claim 12, further comprising:
   detecting the change in the density from the emulsion mixture; and
   calculating density values using Archimedes' principle.

18. The method of claim 17, further comprising calculating density values for each emulsion mixture and demulsifier from the plurality of demulsifiers.

19. The method of claim 18, further comprising processing the density values for each emulsion mixture and demulsifier using the data acquisition and processing system.

20. The method of claim 19, further comprising displaying the change in density values over time for each emulsion mixture and demulsifier on the user interface.

* * * * *

UNITED STATES PATENT AND TRADEMARK OFFICE
CERTIFICATE OF CORRECTION

| | | |
|---|---|---|
| PATENT NO. | : 12,072,346 B2 | Page 1 of 1 |
| APPLICATION NO. | : 17/550906 | |
| DATED | : August 27, 2024 | |
| INVENTOR(S) | : Nagoorpitchai S. Meeranpillai, Ali Almuhaimeed and Osama Alzahrani | |

It is certified that error appears in the above-identified patent and that said Letters Patent is hereby corrected as shown below:

On the Title Page

Column 2, Line 8, (item (57) Abstract), please replace "chamber" with -- chamber; --

In the Claims

In Column 14, Line 4, Claim 2, please replace "probe sensor" with -- probe --

Signed and Sealed this
Fifteenth Day of October, 2024

Katherine Kelly Vidal
*Director of the United States Patent and Trademark Office*